United States Patent
Von Arx et al.

(10) Patent No.: US 7,615,012 B2
(45) Date of Patent: Nov. 10, 2009

(54) BROADBAND ACOUSTIC SENSOR FOR AN IMPLANTABLE MEDICAL DEVICE

(75) Inventors: Jeffrey A. Von Arx, Minneapolis, MN (US); Keith R. Maile, New Brighton, MN (US); Abhi V. Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 395 days.

(21) Appl. No.: 11/212,176

(22) Filed: Aug. 26, 2005

(65) Prior Publication Data

US 2007/0049977 A1    Mar. 1, 2007

(51) Int. Cl.
*A61B 5/02* (2006.01)

(52) U.S. Cl. ..................................... 600/528

(58) Field of Classification Search .............. 607/2, 607/19, 57; 600/528
See application file for complete search history.

(56) References Cited

U.S. PATENT DOCUMENTS

| | | |
|---|---|---|
| 2,967,957 A | 1/1961 | Massa |
| 3,568,661 A | 3/1971 | Franklin |
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,832,580 A | 8/1974 | Yamamuro et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |
| 4,051,455 A | 9/1977 | Fowler |
| 4,056,742 A | 11/1977 | Tibbetts |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |

(Continued)

FOREIGN PATENT DOCUMENTS

EP    0798016    10/1997

(Continued)

OTHER PUBLICATIONS

International Search Report and Written Opinion of International Application No. PCT/US2006/033273, filed Aug. 25, 2006, both mailed Jan. 19, 2007.

(Continued)

*Primary Examiner*—Mark W Bockelman
*Assistant Examiner*—Roland Dinga
(74) *Attorney, Agent, or Firm*—Faegre & Benson LLP

(57) ABSTRACT

An implantable medical device (IMD) is adapted for detecting acoustic chest sounds. The IMD includes a pulse generator having a compartment, the compartment defining an isolated cavity bounded by a back wall. A diaphragm is disposed over and encloses the cavity. An acoustic sensor adapted to sense chest sounds and generate a signal is disposed between the diaphragm and the back wall. The IMD also includes a control circuit disposed within the pulse generator. The circuit is operatively coupled to the acoustic sensor and is adapted to receive the signal.

27 Claims, 5 Drawing Sheets

U.S. PATENT DOCUMENTS

| | | |
|---|---|---|
| 4,227,407 A | 10/1980 | Drost |
| 4,281,484 A | 8/1981 | Massa |
| 4,431,873 A | 2/1984 | Dunn et al. |
| 4,433,400 A | 2/1984 | De Reggi et al. |
| 4,456,850 A | 6/1984 | Inoue et al. |
| 4,481,950 A | 11/1984 | Duggan |
| 4,517,665 A | 5/1985 | De Reggi et al. |
| 4,519,401 A | 5/1985 | Ko et al. |
| 4,541,431 A | 9/1985 | Ibrahim et al. |
| 4,558,249 A | 12/1985 | Lerch et al. |
| 4,580,074 A | 4/1986 | Gilman |
| 4,593,703 A | 6/1986 | Cosman |
| 4,600,855 A | 7/1986 | Strachan |
| 4,642,508 A | 2/1987 | Suzuki et al. |
| 4,653,036 A | 3/1987 | Harris et al. |
| 4,653,508 A | 3/1987 | Cosman |
| 4,660,568 A | 4/1987 | Cosman |
| 4,672,976 A | 6/1987 | Kroll |
| 4,676,255 A | 6/1987 | Cosman |
| 4,677,337 A | 6/1987 | Kleinschmidt et al. |
| 4,781,715 A | 11/1988 | Wurzel |
| 4,793,825 A | 12/1988 | Benjamin et al. |
| 4,835,435 A | 5/1989 | Yeung et al. |
| 4,846,191 A | 7/1989 | Brockway et al. |
| 4,911,172 A | 3/1990 | Bui et al. |
| 4,958,100 A | 9/1990 | Crawley et al. |
| 5,012,815 A | 5/1991 | Bennett, Jr. et al. |
| 5,024,224 A | 6/1991 | Engebretson |
| 5,088,576 A | 2/1992 | Potthoff et al. |
| 5,113,859 A | 5/1992 | Funke |
| 5,160,870 A | 11/1992 | Carson et al. |
| 5,178,153 A | 1/1993 | Einzig |
| 5,283,397 A | 2/1994 | Pavlovic |
| 5,289,821 A | 3/1994 | Swartz |
| 5,300,875 A | 4/1994 | Tuttle |
| 5,314,457 A | 5/1994 | Jeutter et al. |
| 5,339,290 A | 8/1994 | Greenstein |
| 5,367,500 A | 11/1994 | Ng |
| 5,381,067 A | 1/1995 | Greenstein et al. |
| 5,381,386 A | 1/1995 | Lum et al. |
| 5,410,587 A | 4/1995 | Grunwell |
| 5,411,551 A | 5/1995 | Winston et al. |
| 5,423,334 A | 6/1995 | Jordan |
| 5,438,553 A | 8/1995 | Wilson et al. |
| 5,476,488 A | 12/1995 | Morgan et al. |
| 5,483,501 A | 1/1996 | Park et al. |
| 5,488,954 A | 2/1996 | Sleva et al. |
| 5,495,137 A | 2/1996 | Park et al. |
| 5,554,177 A | 9/1996 | Kieval et al. |
| 5,562,714 A | 10/1996 | Grevious |
| 5,571,152 A | 11/1996 | Chen et al. |
| 5,628,782 A | 5/1997 | Myers et al. |
| 5,679,026 A | 10/1997 | Fain et al. |
| 5,704,352 A | 1/1998 | Tremblay et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,757,104 A | 5/1998 | Getman et al. |
| 5,792,195 A | 8/1998 | Carlson et al. |
| 5,807,258 A | 9/1998 | Cimochowski et al. |
| 5,825,117 A | 10/1998 | Ossmann et al. |
| 5,832,924 A | 11/1998 | Archibald et al. |
| 5,833,603 A | 11/1998 | Kovacs et al. |
| 5,843,135 A | 12/1998 | Weijand et al. |
| 5,873,835 A | 2/1999 | Hastings et al. |
| 5,879,283 A | 3/1999 | Adams et al. |
| 5,935,081 A | 8/1999 | Kadhiresan |
| 5,956,292 A | 9/1999 | Bernstein |
| 5,957,950 A | 9/1999 | Mockros et al. |
| 5,967,986 A | 10/1999 | Cimochowski et al. |
| 6,044,298 A | 3/2000 | Salo et al. |
| 6,053,873 A | 4/2000 | Govari et al. |
| 6,058,329 A | 5/2000 | Salo et al. |
| 6,068,589 A | 5/2000 | Neukermans |
| 6,082,367 A | 7/2000 | Greeninger et al. |
| 6,140,740 A | 10/2000 | Porat et al. |
| 6,185,452 B1 | 2/2001 | Schulman et al. |
| 6,223,081 B1 | 4/2001 | Kerver |
| 6,409,675 B1 | 6/2002 | Turcott |
| 6,475,170 B1 | 11/2002 | Doron et al. |
| 6,477,406 B1 * | 11/2002 | Turcott ..................... 600/518 |
| 6,480,733 B1 | 11/2002 | Turcott |
| 6,486,588 B2 | 11/2002 | Doron et al. |
| 6,527,729 B1 | 3/2003 | Turcott |
| 6,537,200 B2 | 3/2003 | Leysieffer et al. |
| 6,554,761 B1 | 4/2003 | Puria et al. |
| 6,575,894 B2 | 6/2003 | Leysieffer et al. |
| 6,600,949 B1 | 7/2003 | Turcott |
| 6,628,989 B1 | 9/2003 | Penner et al. |
| 6,629,922 B1 | 10/2003 | Puria et al. |
| 6,643,548 B1 | 11/2003 | Mai et al. |
| 6,645,145 B1 | 11/2003 | Dreschel et al. |
| 6,654,638 B1 | 11/2003 | Sweeney |
| 6,671,550 B2 | 12/2003 | Iaizzo et al. |
| 6,697,674 B2 | 2/2004 | Leysieffer |
| 6,740,076 B2 | 5/2004 | Hoben et al. |
| 6,741,714 B2 | 5/2004 | Jensen |
| 6,763,722 B2 | 7/2004 | Fjield et al. |
| 6,764,446 B2 | 7/2004 | Wolinsky et al. |
| 7,016,739 B2 | 3/2006 | Bange et al. |
| 7,024,248 B2 | 4/2006 | Penner et al. |
| 7,035,684 B2 | 4/2006 | Lee |
| 7,107,103 B2 | 9/2006 | Schulman et al. |
| 7,220,232 B2 | 5/2007 | Suorsa et al. |
| 7,228,175 B2 | 6/2007 | Jain et al. |
| 7,236,821 B2 | 6/2007 | Cates |
| 7,283,874 B2 | 10/2007 | Penner |
| 7,335,169 B2 | 2/2008 | Thompson et al. |
| 2002/0027400 A1 | 3/2002 | Toda |
| 2002/0036446 A1 | 3/2002 | Toda et al. |
| 2002/0151938 A1 * | 10/2002 | Corbucci ..................... 607/25 |
| 2002/0177782 A1 | 11/2002 | Penner |
| 2003/0055461 A1 | 3/2003 | Girouard et al. |
| 2003/0204165 A1 * | 10/2003 | Houben et al. ........... 604/93.01 |
| 2004/0015104 A1 * | 1/2004 | Goldberger ..................... 601/2 |
| 2004/0103906 A1 | 6/2004 | Schulman et al. |
| 2004/0106954 A1 | 6/2004 | Whitehurst et al. |
| 2004/0106960 A1 | 6/2004 | Siejko et al. |
| 2004/0106961 A1 | 6/2004 | Siejko et al. |
| 2004/0122315 A1 | 6/2004 | Krill |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0147969 A1 * | 7/2004 | Mann et al. ..................... 607/17 |
| 2004/0167416 A1 * | 8/2004 | Lee ............................. 600/513 |
| 2004/0172083 A1 * | 9/2004 | Penner ........................ 607/35 |
| 2004/0204744 A1 | 10/2004 | Penner et al. |
| 2004/0230249 A1 | 11/2004 | Haefner |
| 2005/0102001 A1 | 5/2005 | Maile et al. |
| 2005/0131472 A1 | 6/2005 | Ding et al. |
| 2005/0137490 A1 | 6/2005 | Scheiner et al. |
| 2005/0148896 A1 | 7/2005 | Siejko et al. |
| 2005/0149136 A1 | 7/2005 | Siejko et al. |
| 2005/0149138 A1 | 7/2005 | Min et al. |
| 2006/0009818 A1 | 1/2006 | Von Arx et al. |
| 2006/0082259 A1 | 4/2006 | Schlenke |
| 2006/0142819 A1 | 6/2006 | Penner et al. |
| 2006/0149329 A1 * | 7/2006 | Penner ........................ 607/32 |
| 2008/0021289 A1 | 1/2008 | Zhang et al. |
| 2008/0021509 A1 | 1/2008 | Mi et al. |

2008/0021510 A1 1/2008 Mi et al.

FOREIGN PATENT DOCUMENTS

| EP | 0897690 | 2/1999 |
|---|---|---|
| EP | 1151719 | 11/2001 |
| WO | WO 83/03345 | 10/1983 |
| WO | WO 97/01986 | 1/1997 |
| WO | WO 97/33513 | 9/1997 |
| WO | 9735636 | 10/1997 |
| WO | WO 97/47236 | 12/1997 |
| WO | WO 98/26716 | 6/1998 |
| WO | WO 98/29030 | 7/1998 |
| WO | WO 99/26530 | 6/1999 |
| WO | WO 99/59460 | 11/1999 |
| WO | WO 00/16686 | 3/2000 |
| WO | WO 03/068047 | 8/2003 |
| WO | 2004091719 | 10/2004 |
| WO | WO 2006/069215 | 6/2006 |

OTHER PUBLICATIONS

Robert D. Blevins, Ph.D.., Formulas for Natural Frequency and Mode Shape, ISBN: 1-57524-184-6.

Search Report and Written Opinion of PCT/US2007/073989, filed Jul. 20, 2007, both mailed Dec. 20, 2007.

Search Report and Written Opinion of PCT/US2007/073998, filed Jul. 20, 2007, both mailed Mar. 6, 2008.

C. Hierold et al (Germany, 1998) "Implantable Low Power Integrated Pressure Sensor System for Minimal Invasive Telemetric Patient Monitoring" IEEE, pp. 568-573.

Cassereau et al., "Time Reversal of Ultrasonic Fields—Part 3: Theory of the Closed Time-Reversal Cavity," IEEE Transactions on Ultrasonics, Ferroelectrics, and Frequency Control, vol. 39, No. 5, Sep. 1992, pp. 579-592.

Er. Cosman et al (Massachussetts, Apr. 1979) "A Telemetric Pressure Sensor for Ventricular Shunt Systems" Surgical Neurology, vol. 11, No. 4, pp. 287-294.

Fink et al., "Time Reversal Acoustics," 2004 IEEE Transactions on Ultrasonics, Ferroelectrics, and Frequency Control Joint 50th Anniversary Conference, Ultrasonics Symposium, pp. 850-859.

Fink, "Time Reversal of Ultrasonic Fields—Part 1: Basic Principles," IEEE Transactions on Ultrasonics, Ferroelectrics, and Frequency Control, vol. 39, No. 5, Sep. 1992, pp. 555-566.

G. W. H. Schurink et al (1998) "Late Endoleak after Endovascular Therapy for Abdominal Aortic Aneurysm" Eur. J. Vasc. Endovasc. Surg. vol. 17, pp. 448-450.

GH White et al (1997) "Endoleak Following Endoluminal Repair of AAA: Management Options and Patient Outcomes", J. Endovasc Surg. p. 1-45.

Karl E. Richard et al (Germany, Jan. 1999) "First clinical results with a telemetric shunt-integrated ICP-sensor" Neurological Research vol. 21, pp. 117-120.

Prof. Dr. Johannes Zacheja et al (Germany, Sep. 1996) "An Implantable Microsystem for Biomedical Applications" Micro System Technologies 96, pp. 717-722.

S. K. Gupta et al (1999) "Use of a Piezoelectric Film Sensor for Monitoring Vascular Grafts" The American Journal of Surgery vol. 160, pp. 182-186.

T. Chuter et al (Sweden, Jan. 1997) "Aneurysm Pressure following Endovascular Exclusion" Eur. J. Vasc. Endovasc. Surg. vol. 13, pp. 85-87.

T.A. Cochran et al (1990) "Aortic Aneurysm Abdominal", Current Therapy in Adult Medicine, Fourth Edition.

Wu et al., "Time Reversal of Ultrasonic Fields—Part 2: Experimental Results," IEEE Transactions on Ultrasonics, Ferroelectrics, and Frequency Control, vol. 39, No. 5, Sep. 1992, pp. 567-578.

Z. Tang et al (May 1995) "Data Transmission from an Implantable Biotelemeter by Load-Shift Keying Using Circuit Configuration Modulator" IEEE Transactions on Biomedical Engineering, vol. 42, No. 5, pp. 524-528.

* cited by examiner

BROADBAND ACOUSTIC SENSOR FOR AN IMPLANTABLE MEDICAL DEVICE

PARTIES TO A JOINT RESEARCH AGREEMENT

The claimed invention was made subject to a joint research agreement between Cardiac Pacemakers, Inc. and Remon Medical Technologies Ltd.

TECHNICAL FIELD

The present invention relates to sensors used in combination with a cardiac function management device such as a heart pacemaker or defibrillator to monitor and control the rhythm of the heart. The present invention more particularly relates to sensors used to detect heart sounds and methods of modifying therapy based on these heart sounds.

BACKGROUND

Cardiac function management systems are used to treat heart arrhythmias. Pacemaker systems are commonly implanted in patients to treat bradycardia (i.e., abnormally slow heart rate). A pacemaker system includes an implantable pulse generator and leads, which form the electrical connection between the implantable pulse generator and the heart. An implantable cardioverter defibrillator ("ICD") is used to treat tachycardia (i.e., abnormally rapid heart rate). An ICD also includes a pulse generator and leads that deliver electrical energy to the heart. These systems are also useful in the treatment of heart failure, which is often caused by bundle branch block that can disrupt synchrony between the right and left ventricles. For example, cardiac resynchronization therapy ("CRT") (also commonly referred to as biventricular pacing) is an emerging treatment for heart failure, which involves stimulation of both the right and the left ventricles to increase hemodynamic efficiency and cardiac output.

The beating heart produces a series of auditory vibrations (i.e., heart sounds) that can be characterized by intensity, frequency, quality, and timing with respect to the cardiac cycle. Two of the normal heart sounds, commonly known as the S1 and S2 sounds, relate to closing of various heart valves. Specifically, the S1 sound is generated by the closing of the mitral and tricuspid valves and thus generally correlates to the onset of ventricular systole, and the S2 sound is generated by the closing of the pulmonary and aortic valves and thus generally correlates to the onset of ventricular diastole. These sounds may also indicate problems or abnormalities in the pumping process, such as for example a murmur or mitral regurgitation. There is thus a need for a cardiac rhythm management device that includes a sensor for sensing heart sounds.

SUMMARY

The present invention, according to one embodiment, is an implantable medical device (IMD) including a pulse generator having a compartment, which defines an isolated cavity bounded by a back wall. A compartment diaphragm is disposed over and encloses the cavity. An acoustic sensor adapted to sense chest sounds and generate a signal is disposed between the diaphragm and the back wall. A control circuit disposed within the pulse generator is operatively coupled to the acoustic sensor and is adapted to receive the signal.

According to another embodiment, the present invention is an implantable medical device (IMD) including a pulse generator; a sensor module located remotely from the pulse generator, the sensor module defining a compartment having a compartment diaphragm, an acoustic sensor adapted to sense chest sounds and generate a signal, the acoustic sensor located in the compartment, and a control circuit disposed within the pulse generator, the circuit operatively coupled to the acoustic sensor and adapted to receive the signal.

The present invention, according to yet another embodiment, is a cardiac function management (CFM) system for effecting operation of a human heart. The system includes a pulse generator having a compartment, the compartment defining an isolated cavity bounded by a back wall. A compartment diaphragm is disposed over and enclosing the cavity. An acoustic sensor adapted to sense chest sounds and generate a first signal is disposed between the compartment diaphragm and the back wall. A cardiac lead has an electrode and is adapted to sense electrical activity of the heart. A control circuit is disposed within the pulse generator and is operatively coupled to the acoustic sensor and the cardiac lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
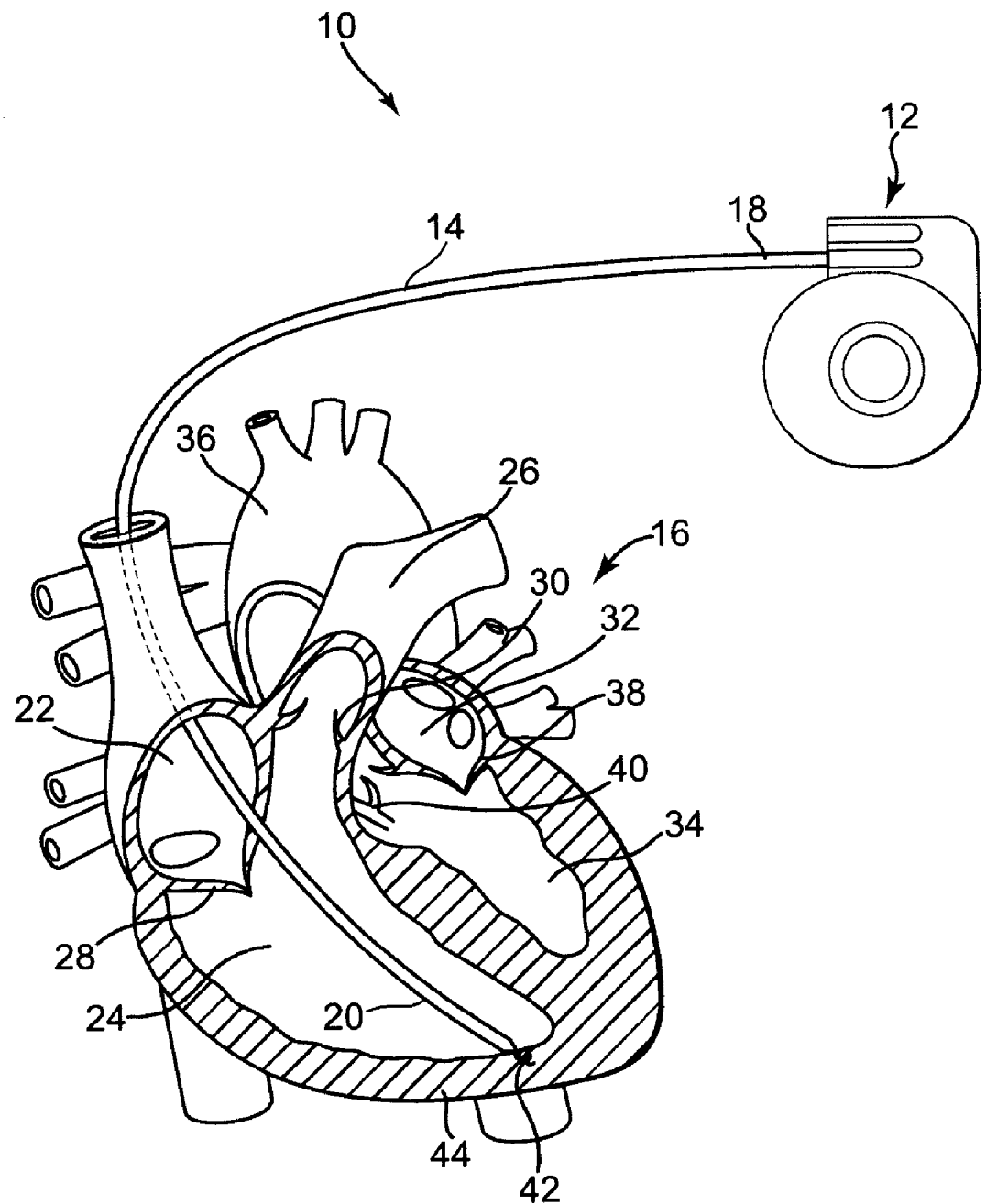
FIG. 1 shows a perspective view of a cardiac rhythm management device according to the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable medical device (IMD) or cardiac function management (CFM) system 10. The system 10 includes a pulse generator 12 and a cardiac lead 14. The lead 14 operates to convey electrical signals between the heart 16 and the pulse generator 12. A proximal end 18 of the lead 14 is coupled to the pulse generator 12 and a distal end 20 is coupled to the heart 16. The lead 14 includes a lead body extending from the lead proximal end 18 to the lead distal end 20.

The heart 16 includes a right atrium 22, a right ventricle (RV) 24, and a pulmonary artery 26. A tricuspid valve 28 is located between and controls the flow of blood from the right atrium 22 and the right ventricle 24. A pulmonic valve 30 is located between and controls the flow of blood from the right ventricle 24 to the pulmonary artery 26. The heart 16 also includes a left atrium 32, a left ventricle (LV) 34, and an aorta 36. A mitral valve 38 is located between and controls the flow of blood from the left atrium 32 to the left ventricle 34. A aortic valve 40 is located between and controls the flow of blood from the left ventricle 34 to the aorta 36. In one embodiment, the CFM system 10 includes a plurality of leads 14. For example, it may include a first lead 14 in communication with the left ventricle 34 and a second lead in communication with the right ventricle 24.

The heart sound S1 is generated when the mitral valve 38 and the tricuspid valve 28 close. The S1 sound is referred to as the "lub" part of the "lub-dub" rhythm of the heart. The heart sound S2 is generated when the pulmonic valve 30 and the aortic valve 40 close and is referred to as the "dub" sound. The S3 heart sound is known to be a ventricular diastolic filling sound often indicative of certain pathological conditions including heart failure, and the S4 heart sound is known to be a ventricular diastolic filling sound resulting from atrial contraction and is also usually indicative of pathological conditions. The phrase "heart sound," as used herein refers to any sound made by the heart during operation, including any of S1, S2, S3, S4, or any components thereof. Other notable heart sounds include that of mitral regurgitation (MR). The phrase "chest sound," as used herein includes heart sounds as well as lung sounds and any other sounds that may be present in a patient's chest cavity. Common lung sounds of interest include coughs, rales and wheezes. Other chest sounds may include, for example, snoring and talking.

In the embodiment shown in FIG. 1, a helical electrode 42 penetrates the endocardium of the RV 24 and is embedded in the myocardium 44 of the heart 16. When positioned as above, the electrode 42 can be used to sense the electrical activity of the heart 16 or to apply a stimulating pulse to the left ventricle 34. In other embodiments, the cardiac lead 14 of the present invention can also be implanted in any other portion of the heart 16 as known in the art of cardiac function management. For example, it may be implanted in the right atrium 22, the right ventricle 24, the pulmonary artery 26, the left ventricle 34, or in the coronary veins. In one embodiment, the system 10 includes multiple electrodes 42 disposed to sense electrical activity and/or deliver therapy to both the left and right sides of the heart 16.

Figure 2A:
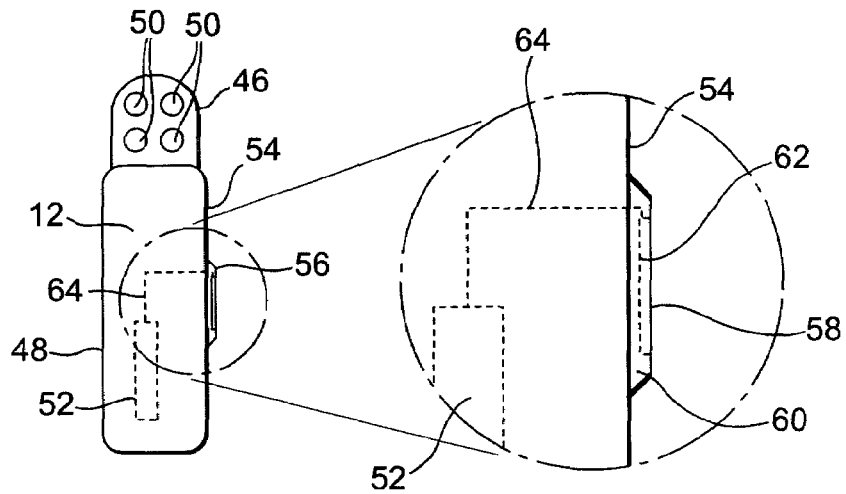
FIGS. 2A-2C show various views of a cardiac rhythm management device having an acoustic sensor according to one embodiment of the present invention.
Figure 2B:
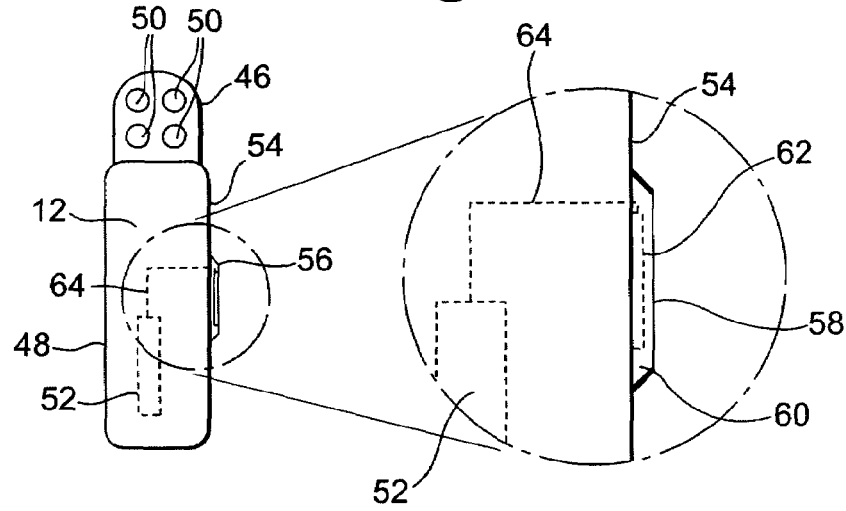

FIGS. 2A and 2B show side views of the pulse generator 12 according to embodiments of the present invention. As shown in FIG. 2A, the pulse generator 12 includes a header 46 and a housing 48. The header 46 includes connectors 50 for connecting to the lead 14. The housing 48 encloses circuitry 52 and includes an outer wall or substantially planar face 54.

As shown in FIG. 2B, a coin or compartment 56 is located on the planar face 54. The compartment 56 may protrude from the planar face 54 (in which case the back wall of the compartment 56 is the substantially planar face 54 of the housing 48) or may be inset into the housing 48. The compartment 56 includes a compartment diaphragm 58 and a cavity 60 located behind the compartment diaphragm 58 (shown in the enlarged section of FIG. 2A). An acoustic sensor 62 is located in the cavity 60 between the compartment diaphragm 58 and back wall of the compartment 56. In the embodiment where the compartment 56 is inset into the housing, the compartment diaphragm 58 is generally flush with the face of the surrounding wall of the housing 48. In one embodiment, the cavity 60 contains a fluid or gel having an acoustic impedance that is generally an acoustic match to that of the body in which it is implanted. This fluid or gel may be any substance generally known in the art having an impedance that generally matches that of the human body, such as for example water or an ultrasound gel.

Figure 2C:
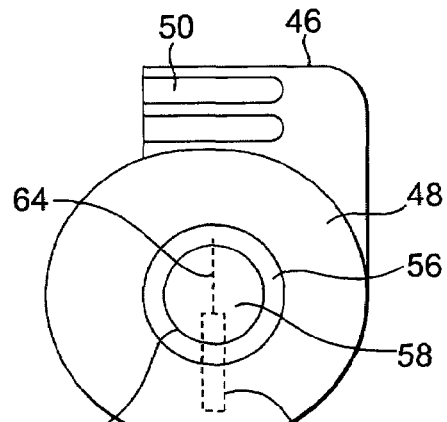

In the embodiment shown in FIGS. 2A-2C, the cavity 60 is hermetically sealed. The housing 48 is comprised of titanium and may for example have a thickness of about 0.010 inch. The compartment diaphragm 58 is also comprised of titanium and has a thickness less than the thickness of the housing. Reducing the thickness of the compartment diaphragm 58 allows acoustic energy to vibrate the compartment diaphragm 58 more easily. In one embodiment, the compartment diaphragm 58 has a thickness of between about 0.002 inch and about 0.010 inch. In one embodiment, the resonant frequency of the compartment diaphragm 58 is much higher than the acoustic frequencies of interest in order to ensure a reasonably flat acoustic response over frequency. In one embodiment, for example, the resonant frequency of the compartment diaphragm 58 is greater than about 20,000 Hz.

The acoustic sensor 62 is adapted to sense broadband chest sounds, which may include for example heart and lung sounds such as S2 splitting, mitral regurgitation, coughs, rales, and wheezes. Other chest sounds, which may be detected by the acoustic sensor 62 include Gallop sounds, snoring and a patient's voice. The acoustic sensor 62 is electrically connected to the circuitry 52 by one or more feedthroughs 64. The sensor 62 may have, for example, a broadband acoustic range of from about 10 to about 20,000 Hz. In one embodiment, the range of the sensor 62 is from about 100 to about 5,000 Hz, and, in yet another embodiment, the range is from about 100 to about 3,000 Hz.

The acoustic sensor 62 can be comprised of any of a variety of microphones known in the art. Exemplary microphones include piezoelectric, piezoresistive, and capacitive-type microphones. The piezoelectric microphone may be made from any piezoelectric material, including piezocomposites, piezoceramics, piezoplastics and the like. The sensor 62 may, for example, be comprised of a piezoelectric film, such as polyvinylidine fluoride (PVDF), which takes the form of a thin plastic polymer sheet and may have a thin electrically conductive nickel copper alloy deposited on each side. The sensor 62 acts as a strain gage that generates an electrical signal when the compartment diaphragm 58 vibrates in response to a heart or lung sound.

In one embodiment, the acoustic sensor 62 is a microelectrical mechanical system (MEMS) device. One such exemplary device is the SiSonic MEMS microphone available from Knowles Acoustics, Inc. (www.knowlesacoustics.com) of Itasca, Ill. A MEMS microphone is fabricated from a silicon chip using standard semiconductor processing techniques. Such a microphone may include a diaphragm and a backplate fabricated from a silicon wafer. In one embodiment, the thickness of the sensor 62 is from about 0.01 to about 2 mm. In another embodiment, the thickness of the sensor 62 is less than about 0.5 mm. The acoustic sensor 62 may have a width dimension and a length dimension each between about 1 and about 2 mm.

FIGS. 2A and 2B illustrative two exemplary locations for the sensor 62 in the cavity 60. As shown in FIG. 2A, the sensor 62 is coupled to the compartment diaphragm 58. In this embodiment, the diaphragm of the sensor 62 may be mechanically coupled to the compartment diaphragm 58. In one exemplary embodiment, a piezoelectric or piezoresistive material is attached to an inner surface of the compartment diaphragm 58 using an epoxy or a medical adhesive as is known in the art.

As shown in FIG. 2B, the sensor 62 is located on the back wall of the compartment 56, which is defined by the planar face 54 of the housing 48. In this embodiment, the sensor 62 may include an opening to allow the portion of the sensor 62 located between the diaphragm and the planar face 54 to communicate with the remainder of the cavity 60, which minimizes acoustic dampening in the sensor 62. In the embodiment of FIG. 2B, the diaphragm of the acoustic sensor 62 is separated from the compartment diaphragm 58 by a small distance. As noted above, this separation space in the cavity 60 may be filled with a fluid having an appropriate acoustic impedance.

In one embodiment, the acoustic sensor 62 is an accelerometer, including, for example, a piezoelectric crystal accelerometer sensor of the type used by pacemakers to sense the level of activity of the patient. Use of such an accelerometer for detecting heart sounds is described in more detail, for example, in U.S. Publication 2005/0137490 and U.S. Publication 2005/0102001, both of which are hereby incorporated by reference. In another exemplary embodiment, the IMD 10 includes both an accelerometer and a piezoelectric sensor. In this embodiment, the accelerometer is typically located inside the hermetic housing and is generally most effective at sensing lower frequencies, whereas the sensor is in a cavity located behind a diaphragm and is optimized for detecting frequencies above that detected by the accelerometer.

The compartment diaphragm 58 and the compartment 56 can be any shape, including circular, oval, rectangular, or square. In the embodiment shown in FIG. 2C, the compartment diaphragm 58 and the compartment 56 both have a circular shape. The compartment 46 may include a chamfer 66 to avoid irritation of the body tissue adjacent to the compartment 56. In one embodiment, the compartment 56 extends outwardly from the planar face 54, while in other embodiments, the compartment 56 is disposed within or behind the planar face 54.

Figure 3A:
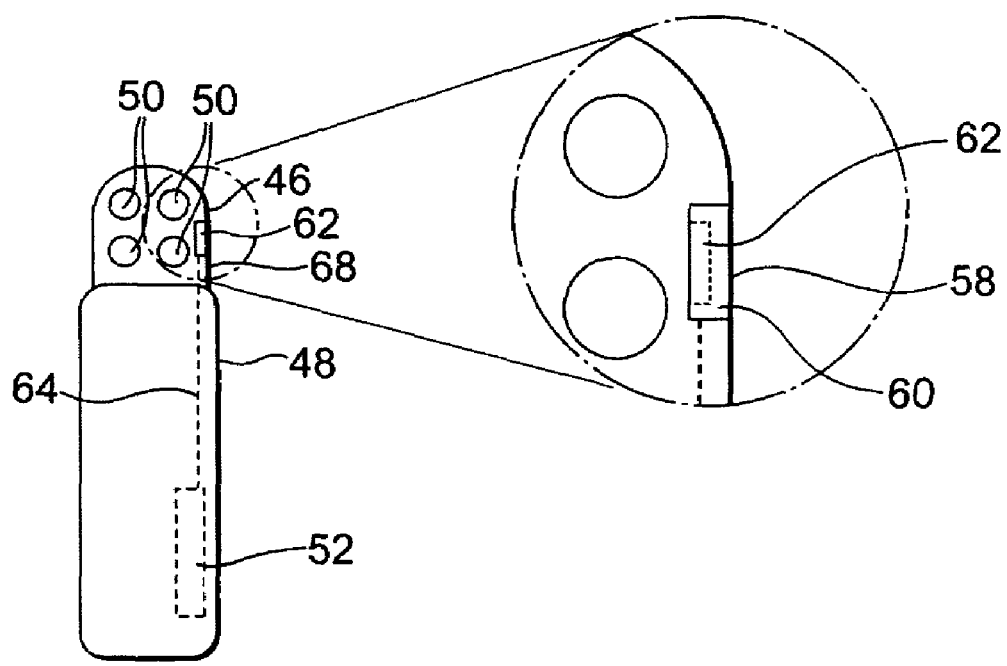
FIGS. 3A-3B show various views of a cardiac rhythm management device having an acoustic sensor according to another embodiment of the present invention.
Figure 3B:
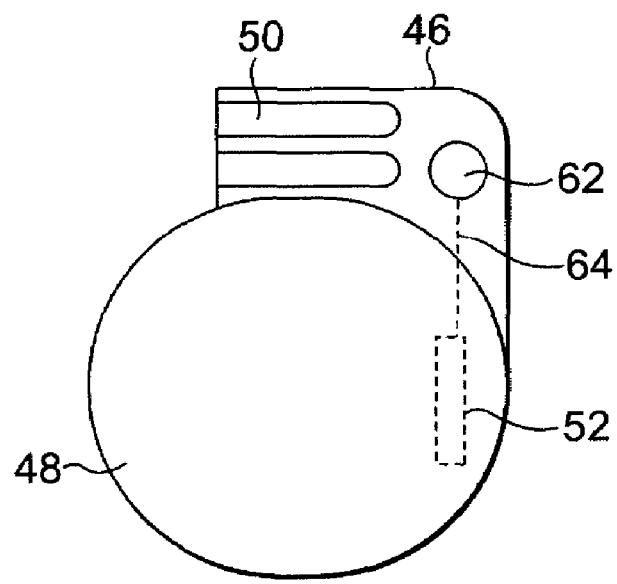

FIGS. 3A-3B show another embodiment of the present invention. As shown, the acoustic sensor 62 is located in a cavity 60 behind an outer surface 68 of the header 46. The header 46 can be comprised of Tecothane or any other suitable material as is known in the art. Sealed hermetic feedthroughs 64 electrically connect the acoustic sensor 62 to the circuitry 52. The acoustic sensor 62 shown in FIGS. 3A-3B is a substantially flat piezoelectric, piezoresistive, or capacitive device (e.g., a MEMS microphone), but in an alternative embodiment, the acoustic sensor 62 could comprise a piezoelectric cylindrical transducer, as is known in the art. In this embodiment, the acoustic sensor 62 may be disposed within a cavity 60 behind the outer surface 68, as described with respect to FIGS. 2A-2B above. Alternatively, the diaphragm of the sensor 62 may be positioned such that it is not covered over by the material that forms the header body (e.g., Tecothane). In both of these embodiments, the sensor 62 is directly exposed to bodily fluids, as the header material is not hermetically sealed and thus is penetrable by bodily fluids.

In one embodiment, the acoustic sensor 62 of FIGS. 3A-3B is contained in a hermetically sealed, titanium tab or housing (e.g., such as is described below with reference to FIGS. 4A and 4B). In this exemplary embodiment, the tab or housing includes a relatively thin diaphragm to allow sound to penetrate the tab and reach the acoustic sensor 62.

Figure 4A:
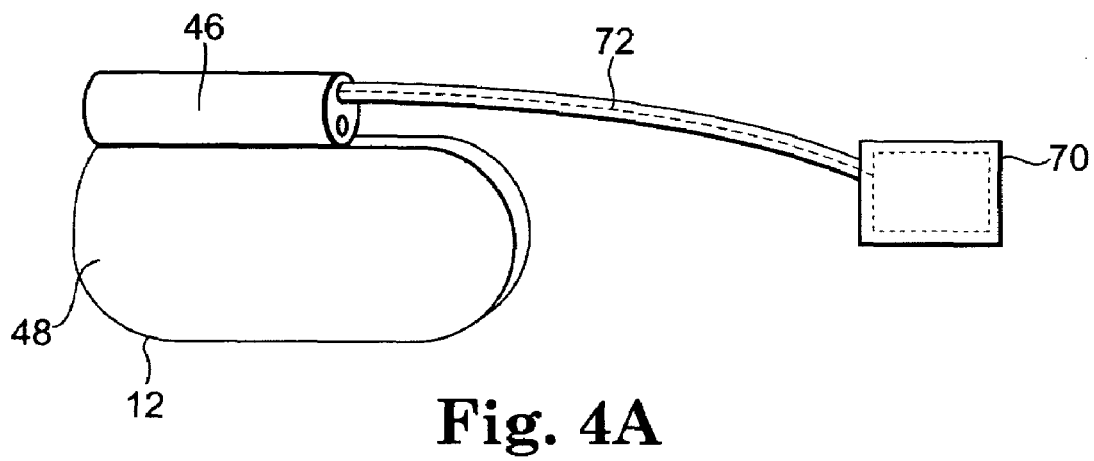
FIGS. 4A-4B show various views of a cardiac rhythm management device having an acoustic sensor according to yet another embodiment of the present invention.
Figure 4B:
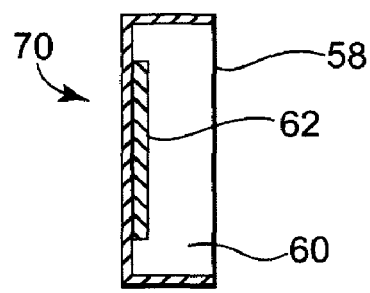

FIGS. 4A-4B show yet another embodiment of the present invention. The acoustic sensor 62 shown in FIGS. 4A-4B is located in a sensor module or tab 70, which is located outside of the pulse generator 12. In one embodiment, as shown in FIG. 4A, the tab 70 is structurally separate from the pulse generator 12. As shown in FIG. 4A, the acoustic sensor 62 is electrically connected to the circuitry 52 via a conductive member 72. In another embodiment, the acoustic sensor 62 is coupled using any wireless communication technique known in the art. The tab 70 can be comprised of titanium and includes a compartment diaphragm 58 and a cavity 60. The tab 70 may be implanted near the patient's heart in a location adapted to detect key heart sounds, such as S1 and S2. As described above with respect to FIGS. 2A and 2B, the sensor 62 may be coupled either to the back wall of the tab 70 or directly to the diaphragm 58. Also as described above, in one embodiment the cavity 60 is filled with a fluid or gel that has an acoustic impedance generally matching that of the body.

Figure 5:
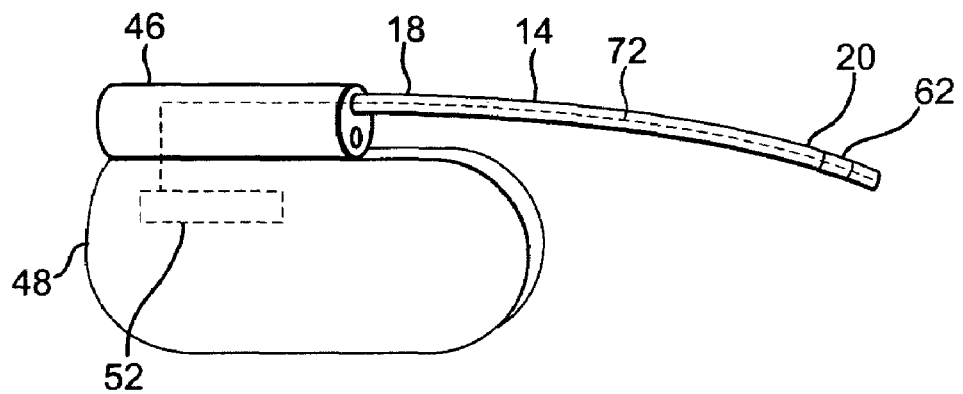
FIG. 5 shows a perspective view of a cardiac rhythm management device having an acoustic sensor according to another embodiment of the present invention.

FIG. 5 shows yet another embodiment of the present invention. In this embodiment, the acoustic sensor 62 may comprise a cylindrical transducer as is known in the art, such as for example a piezoelectric cylindrical transducer. In this embodiment, the sensor 62 may also comprise a generally flat MEMS transducer, as described above. This MEMS transducer may have a variety of shapes, including for example round, oval, rectangular or square. The acoustic sensor 62 is located on the lead 14 near the distal end 20 and is electrically connected to the circuitry 52 via a conductive member 72. In yet another embodiment, the IMD 10 includes more than one acoustic sensor 62. For example, it may include a first acoustic sensor 62 located in the housing 48 (see for example FIG. 2A) and a second acoustic sensor 62 located on a lead (see for example FIG. 5).

Figure 6:
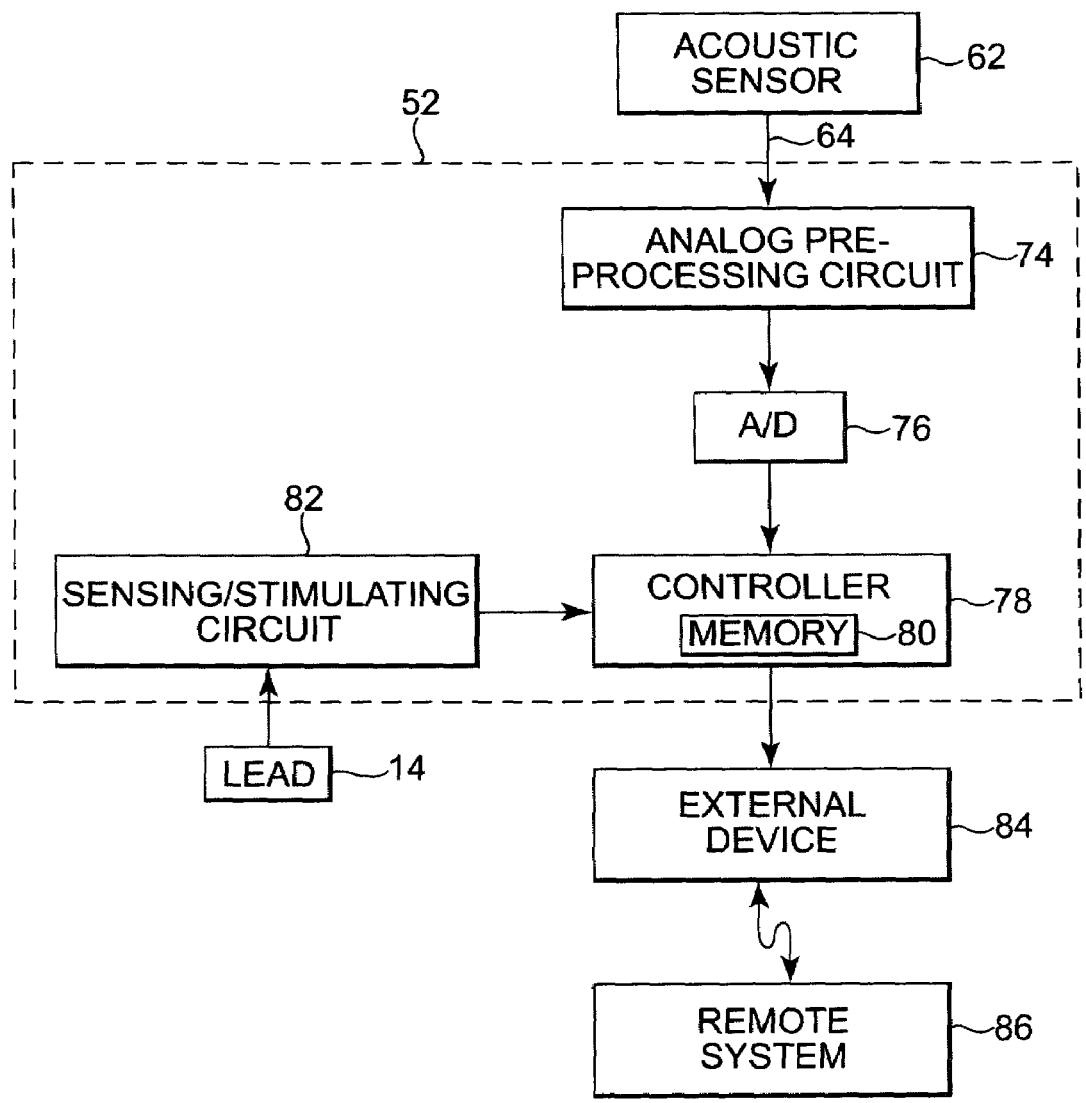
FIG. 6 shows a circuit diagram, for receiving and processing a signal from an acoustic sensor, according to one embodiment of the present invention.

FIG. 6 shows at least a portion of the circuitry 52, for processing the signals received from the acoustic sensor 62, according to one embodiment of the present invention. As shown, the signal (e.g., a voltage) from the acoustic sensor 62 is processed by an analog pre-processing circuit 74, which may include, for example, a filter and/or an amplifier. The analog signal is then converted to a digital signal by an analog-to-digital converter 76. This digital signal is then directed into a microprocessor or controller 78 for analysis. The signals may also be stored in a memory 80 coupled to the controller 78. As further shown in FIG. 6, the circuitry 52 may also include a sensing/stimulating circuit 82 for processing the electrical signals received from or delivered to the lead 14. The circuit 82, in one embodiment, generates an electrocardiogram (ECG), which is provided to the controller 78.

Such a configuration as is shown in FIG. 6 allows the controller 78 to receive and store signals from the acoustic sensor 62 and/or from the lead 14. The controller 78 then analyzes these signals to identify heart sounds (e.g., S1, S2, S3, S4, MR and S2 splitting) and lung sounds (e.g., coughs, rales, and wheezes) and modifies therapy, as appropriate, based on the information these signals provide about the functioning of a patient's heart. In one embodiment, the controller 78 stores and averages several cycles (e.g., 10 cycles) of heart sound data, to help attenuate signal noise. In another embodiment, the controller 78 is programmed to subject the signal to a Fourier transform algorithm, such as a fast Fourier transform (FFT), which may provide for a more efficient technique for identifying certain chest sounds. In one embodiment, the controller 78 initiates this process of receiving signals from the acoustic sensor 62 at a predetermined time interval (e.g., hourly). In other embodiments, the controller 78 continuously receives and evaluates signals from the acoustic sensor 62. In another embodiment, the process is initiated upon detection of some pre-specified condition, such as for example the detection by the controller 78 of a cardiac arrhythmia.

Several techniques for identifying a specified chest sounds may be employed, including, for example, analyzing the signal from the acoustic sensor 62 to identify the presence of a signal exceeding a certain amplitude within a certain frequency range and within a specified portion of the cardiac cycle. In one embodiment, a specified chest sound is identified by comparing the signal to an acoustic template representing a "normal" condition or to sounds previously recorded for that particular patient. These previously recorded sounds could, for example, be stored during an examination by a physician, after the physician confirms acceptable heart function. In one embodiment, the ECG information is used to further assist in detecting a specified heart sound. The ECG information, for example, may be used to "window" a certain portion of the acoustic data, based on knowledge of a skilled artisan relating to the location in the cardiac cycle during which a specified sound is likely to occur. Exemplary techniques for identifying a specified heart sound and for correlating the acoustic data to a certain location in the cardiac cycle is disclosed in commonly-assigned U.S. Publication 2004/0106961, which is hereby incorporated by reference.

In one embodiment, the circuitry 52 further includes a logbook feature. In this embodiment, for example, the controller 78 may operate to store a predetermined time period of data in a specified area of the memory 80 periodically, or it may operate to store a specified time period of data only upon detection of an abnormal condition. This feature then allows a user to access this stored data at a later time for additional analysis.

In one embodiment, the system further includes an external device 84, which is operatively coupled to the circuitry 52 by, for example, a wireless RF communication link. The external device 84 may, for example, be an external programmer adapted for use with the implanted medical device 10. This external device 84 is, in turn, coupled to a remote system 86. The external device 84 and remote system 86 may, for example, be coupled by a telephone line, electrical or optical cable, RF interface, satellite link, local area network or wide area network. The remote system 86 allows a user (e.g., a physician) located at a remote location to obtain data relating to the heart sounds and to conduct or aid in the diagnosis of a patient based on such data. In one embodiment, the remote system 86 includes an advanced patient management system, such as is disclosed in U.S. Publication 2004/0122484, which is hereby incorporated by reference in its entirety.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. An implantable medical device (IMD) comprising:
   a pulse generator having a housing and a compartment, the compartment being disposed on an outer surface of a wall of the housing and defining an isolated, hermetically sealed cavity bounded by a back wall;
   a compartment diaphragm with a resonance frequency greater than about 20 kHz disposed over and enclosing the cavity, the isolated cavity having an inner surface;
   an acoustic sensor having a sensor diaphragm, the sensor adapted to sense chest sounds having a frequency from about 10 Hz to about 20 kHz and generate a signal, the sensor disposed on an inner surface of the compartment diaphragm; and
   a control circuit disposed within the housing, the circuit operatively coupled to the acoustic sensor and adapted to receive the signal.

2. The IMD of claim 1 wherein an acoustic range of the acoustic sensor is from about 100 to about 5,000 Hz.

3. The IMD of claim 2 further comprising an accelerometer operatively coupled to the control circuit.

4. The IMD of claim 2 wherein the acoustic sensor includes an amplifier for amplifying the signal detected by the acoustic sensor.

5. The IMD of claim 1 wherein the acoustic sensor is a piezoresistive sensor or a capacitive sensor.

6. The IMD of claim 1 wherein the acoustic sensor is a MEMS microphone.

7. The IMD of claim 1 wherein the sensor diaphragm of the acoustic sensor is made from a piezoelectric material.

8. The IMD of claim 7 wherein the piezoelectric material comprises a piezoceramic material.

9. The IMD of claim 7 wherein the sensor diaphragm is attached to the compartment diaphragm using an epoxy or medical adhesive.

10. The IMD of claim 1 wherein the pulse generator includes a housing and a header.

11. The IMD of claim 10 wherein the compartment extends outwardly from a housing outer wall and further wherein the back wall is formed by the housing outer wall.

12. The IMD of claim 10 wherein the electrical connection between the acoustic sensor and the controller includes a hermetically sealed feedthrough.

13. The IMD of claim 1 wherein the compartment diaphragm is located on a side of the compartment facing away from the pulse generator housing.

14. The IMD of claim 1, wherein the sensor is disposed between the compartment diaphragm and the back wall such that a space is maintained between the sensor diaphragm and the inner surface of the cavity, the space being filled with a medium, the medium having an acoustic impedance generally matching an acoustic impedance of a body location in which the IMD is implanted.

15. The IMD of claim 14, wherein the medium is a gel having an acoustic impedance generally matching a second acoustic impedance of a body location in which the IMD is implanted.

16. The IMD of claim 1, wherein the back wall of the compartment is defined by the outer wall of the housing.

17. The IMD of claim 1, wherein the compartment diaphragm is less thick than the wall of the housing on which the compartment diaphragm is disposed.

18. The IMD of claim 17, wherein the compartment diaphragm is between 0.002 inches and 0.01 inches thick.

19. The IMD of claim 1, wherein the back wall of the compartment is defined by the outer wall of the housing.

20. The IMD of claim 1, wherein the compartment diaphragm is less thick than the wall of the housing on which the compartment diaphragm is disposed.

21. The IMD of claim 20, wherein the compartment diaphragm is between 0.002 inches and 0.01 inches thick.

22. A cardiac function management (CFM) system for effecting operation of a human heart, the system comprising:
   a pulse generator having a housing and a compartment, the compartment being disposed on an outer surface of a wall of the housing and defining an isolated, hermetically sealed cavity bounded by a back wall;
   a compartment diaphragm with a resonance frequency greater than about 20 kHz disposed over and enclosing the cavity, the isolated cavity having an inner surface;

an acoustic sensor having a sensor diaphragm, the sensor adapted to sense chest sounds having a frequency from about 10 Hz to about 20,000 Hz and generate a first signal, the sensor disposed on an inner surface of the compartment diaphragm;

a cardiac lead having an electrode and adapted to sense electrical activity of the heart; and a control circuit disposed within the pulse generator, the circuit operatively coupled to the acoustic sensor and the cardiac lead.

23. The CFM system of claim 22 further including an accelerometer operatively coupled to the control circuit.

24. The CFM system of claim 22 further including an external device in wireless communication with the control circuit for receiving at least a portion of the first signal.

25. The CFM system of claim 22 further including a remote device in communication with the external device for delivering the first signal to a remote user.

26. The CFM of claim 22 wherein the compartment diaphragm is located on a side of the compartment facing away from the pulse generator housing.

27. The CFM of claim 22, wherein the sensor is disposed between the compartment diaphragm and the back wall such that a space is maintained between the sensor diaphragm and the inner surface of the cavity, the space being filled with a medium, the medium having an acoustic impedance generally matching an acoustic impedance of a body location in which the CFM is implanted.

* * * * *